(12) United States Patent
Beard et al.

(10) Patent No.: US 7,596,078 B2
(45) Date of Patent: Sep. 29, 2009

(54) METHOD AND APPARATUS FOR REDUCING CROSSTALK IN A STRUCTURAL HEALTH MONITORING SYSTEM

(75) Inventors: Shawn J. Beard, Livermore, CA (US); Xinlin Qing, Cupertino, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 620 days.

(21) Appl. No.: 11/271,351

(22) Filed: Nov. 10, 2005

(65) Prior Publication Data

US 2007/0175279 A1 Aug. 2, 2007

(51) Int. Cl.
*G01N 29/04* (2006.01)
*H04J 1/12* (2006.01)

(52) U.S. Cl. .................... 370/201; 370/241; 73/584

(58) Field of Classification Search ............ 370/201, 370/241; 73/584; 438/48
See application file for complete search history.

(56) References Cited

U.S. PATENT DOCUMENTS

| | | | |
|---|---|---|---|
| 3,713,127 A | 1/1973 | Keledy et al. |
| 3,822,586 A | 7/1974 | Pollock |
| 3,858,439 A | 1/1975 | Nakamura |
| 3,924,456 A | 12/1975 | Vahaviolos |
| 3,956,731 A | 5/1976 | Lewis, Jr. |
| 4,006,625 A | 2/1977 | Davis |
| 4,107,981 A | 8/1978 | Kanagawa et al. |
| 5,176,032 A | 1/1993 | Holroyd et al. |
| 5,195,046 A | 3/1993 | Gerardi et al. |
| 5,298,964 A | 3/1994 | Nelson et al. |
| 5,714,687 A | 2/1998 | Dunegan |
| 5,774,376 A | 6/1998 | Manning |
| 5,814,729 A | 9/1998 | Wu et al. |

(Continued)

FOREIGN PATENT DOCUMENTS

| | | |
|---|---|---|
| DE | 4237404 | 5/1994 |
| DE | 19835561 | 2/2000 |
| DE | 10217031 | 10/2003 |

OTHER PUBLICATIONS

Roh, Youn-Seo, et al., "*Effect of Impact Damage on Lamb Wave Propagation in Laminated Composites*" Department of Aeronautics and Astronautics, Stanford University, Stanford, CA 94305 (1995) pp. 1-12.

(Continued)

*Primary Examiner*—Min Jung
(74) *Attorney, Agent, or Firm*—Haynes and Boone, LLP

(57) ABSTRACT

Methods and apparatus for reducing crosstalk in a structural health monitoring system. A pair of actuator input signals are sent to an actuator, each resulting in the transmission of stress waves to a corresponding sensor. The sensor then converts these stress waves to a pair of output signals, each having a crosstalk portion due to electromagnetic interference from the input signals to the actuator, and a stress wave portion corresponding to the stress waves. Various methods of varying the actuator input signals, the input to the actuator, and the output of the sensor result in two output signals that can be combined so as to reduce the crosstalk portions and isolate the stress wave portions. This allows actuators and sensors to be placed sufficiently close together that the stress wave portions of sensor output signals can overlap their crosstalk, without corrupting or otherwise compromising the data contained therein.

16 Claims, 5 Drawing Sheets

U.S. PATENT DOCUMENTS

| | | | | |
|---|---|---|---|---|
| 5,870,239 | A | * | 2/1999 | Furuya .................. 360/55 |
| 5,953,140 | A | * | 9/1999 | McKiel, Jr. ............... 398/79 |
| 6,006,163 | A | | 12/1999 | Lichtenwalner et al. |
| 6,065,342 | A | | 5/2000 | Kerr et al. |
| 6,084,837 | A | * | 7/2000 | Miyanabe et al. ....... 369/53.33 |
| 6,170,334 | B1 | | 1/2001 | Paulson |
| 6,252,334 | B1 | | 6/2001 | Nye et al. |
| 6,370,964 | B1 | | 4/2002 | Chang et al. |
| 6,399,939 | B1 | | 6/2002 | Sundaresan et al. |
| 6,418,384 | B1 | | 7/2002 | Rothea et al. |
| 6,433,463 | B1 | * | 8/2002 | Lal et al. .................. 310/328 |
| 6,529,127 | B2 | | 3/2003 | Townsend et al. |
| 6,691,007 | B2 | | 2/2004 | Haugse et al. |
| 6,693,548 | B2 | | 2/2004 | Boyce et al. |
| 6,768,312 | B2 | | 7/2004 | Sun et al. |
| 6,826,982 | B2 | | 12/2004 | O'Brien et al. |
| 6,964,201 | B2 | | 11/2005 | Xu et al. |
| 7,038,470 | B1 | | 5/2006 | Johnson |
| 7,075,424 | B1 | | 7/2006 | Sundaresan |
| 7,103,507 | B2 | | 9/2006 | Gorinevsky |
| 7,117,742 | B2 | | 10/2006 | Kim |
| 7,118,990 | B1 | | 10/2006 | Xu et al. |
| 7,201,035 | B2 | | 4/2007 | Sunshine |
| 7,246,521 | B2 | | 7/2007 | Kim |
| 7,248,803 | B2 | * | 7/2007 | Kikushima ............... 398/159 |
| 2001/0047691 | A1 | | 12/2001 | Dzenis |
| 2002/0154029 | A1 | | 10/2002 | Watters et al. |
| 2003/1016470 | | | 9/2003 | Goldfine et al. |
| 2004/0002815 | A1 | | 1/2004 | Ishizaki et al. |
| 2004/0032013 | A1 | | 2/2004 | Cobbley et al. |
| 2005/0072249 | A1 | | 4/2005 | Maeda et al. |
| 2006/0042398 | A1 | | 3/2006 | Maubant et al. |
| 2006/0079747 | A1 | | 4/2006 | Beard et al. |
| 2006/0154398 | A1 | | 7/2006 | Qing et al. |
| 2006/1014944 | | | 7/2006 | Baur et al. |
| 2006/0179949 | A1 | | 8/2006 | Kim |
| 2006/0283266 | A1 | | 12/2006 | Qing et al. |
| 2007/0018083 | A1 | | 1/2007 | Kumar et al. |

OTHER PUBLICATIONS

Keilers, Charles Henry Jr., "*Damage identification in Composites Using Built-in Piezoelectrics: A Dissertation Submitted to the Department of Aeronautics and Astronautics and the Committee on Graduate Studies of Stanford University in Partial Fulfillment of the Requirements for the Degree of Doctor of Philosophy*", pp. 1-111 (Jun. 1993).

Roh, Youn-Seo, "*Built-in Diagnostics for Identifying an Anomaly in Plates Using Wave Scattering*", UMI Microform 9924496, UMI Company, ANn Arbor, MI (1999) pp. iv-88.

Chang, Fu-Kuo, "*Built-in Damage Diagnostics for Composite Structures*" Department of Aeronautics and Astronautics, Stanford University, Stanford, CA 94305 (1995).

* cited by examiner

METHOD AND APPARATUS FOR REDUCING CROSSTALK IN A STRUCTURAL HEALTH MONITORING SYSTEM

BRIEF DESCRIPTION OF THE INVENTION

This invention relates generally to structural health monitoring. More specifically, this invention relates to the reduction of crosstalk in structural health monitoring systems.

BACKGROUND OF THE INVENTION

The diagnostics and monitoring of structures, such as that carried out in the structural health monitoring field, are often accomplished by employing arrays of piezoelectric sensing elements and/or actuators. However, such arrays are limited in several respects. As one example, electromagnetic interference, or crosstalk, often places a lower limit on the spacing between actuators and sensors.

To illustrate this concept, FIG. 1 shows the operation of a typical sensor and actuator used in structural health monitoring. Here, an actuator 10 is shown, which is often a piezoelectric transducer capable of changing its shape according to an applied voltage, so as to generate a stress wave, as shown. That is, when attached to a structure, the actuator 10 converts an electrical input signal 20 to a stress wave that propagates through a structure to a sensor 30 placed a distance d away, where it is detected and converted to an electrical output signal 40. However, the sensor 30 also picks up the electromagnetic interference from the input signal 20. Accordingly, the output signal 40 has a crosstalk portion 50 caused by interference from the input signal 20, as well as a stress wave portion 60 corresponding to the detected stress wave. Typically, the signal of interest is the stress wave portion 60, while the crosstalk portion 50 is regarded as a nuisance.

It is known that the amount by which the crosstalk portion 50 and stress wave portion 60 are separated is a function of the distance d between the actuator 10 and sensor 30. That is, as the distance d decreases, the crosstalk portion 50 and stress wave portion 60 move closer together. Conventionally, the minimum distance d that an actuator 10 and sensor 30 can be placed together is the point at which the crosstalk portion 50 and stress wave portion 60 begin to overlap:

$$d_{min} = v_{wave} t_{input} \quad (1)$$

where $d_{min}$=conventional minimum distance $v_{wave}$=velocity of generated stress wave $t_{input}$=time duration of actuator input signal For optimal structural health monitoring, it is often desirable to position actuators closer to sensors than the distance $d_{min}$. However, doing so requires somehow dealing with overlap between the crosstalk portion 50 and stress wave portion 60, as the crosstalk portion 50 alters the stress wave portion 60, commonly resulting in invalid sensor readings. It is therefore desirable to develop methods for reducing crosstalk between actuators and sensors, so as to allow for more densely positioned actuators 10 and sensors 30, and more accurate/reliable structural health monitoring.

SUMMARY OF THE INVENTION

The invention can be implemented in numerous ways, including as a method, an apparatus, and a computer readable medium. Several embodiments of the invention are discussed below.

As a method of monitoring the health of a structure according to stress waves transmitted from an actuator to a sensor through the structure, one embodiment of the invention comprises initiating the transmission of first and second actuation signals to the actuator so as to facilitate the generation of first and second stress waves within the structure. First and second sensor signals are received from the sensor, the sensor signals each having a crosstalk portion corresponding to an electromagnetic interference from the respective actuation signal, and a stress wave portion corresponding to the respective stress wave. The first and second sensor signals are combined so as to isolate the stress wave portions from the crosstalk portions.

In another embodiment of the invention, a computer readable medium has computer executable instructions thereon for a method of monitoring the health of a structure according to stress waves transmitted from an actuator to a sensor through the structure. Here, the method comprises initiating the transmission of first and second actuation signals to the actuator so as to facilitate the generation of first and second stress waves within the structure. First and second sensor signals are received from the sensor, the sensor signals each having a crosstalk portion corresponding to an electromagnetic interference from the respective actuation signal, and a stress wave portion corresponding to the respective stress wave. The first and second sensor signals are combined so as to isolate the stress wave portions from the crosstalk portions.

As a system for monitoring the health of a structure, another embodiment of the invention comprises an actuator configured to generate a stress wave from an actuation signal. Also included is a sensor configured to receive the stress wave and to generate a sensor signal having a first portion corresponding to an electromagnetic interference from the actuation signal, and a second portion corresponding to the stress wave. Also included is a processor in communication with the actuator and the sensor. The actuator and the sensor are configured for placement upon a structure at a distance apart from each other, the distance corresponding to the second portion of the sensor signal overlapping the first portion. Also, the processor is configured to isolate the second portion of the sensor signal from the overlapping first portion.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention, together with further objects and advantages thereof, may best be understood by reference to the following description taken in conjunction with the accompanying drawings in which.

Like reference numerals refer to corresponding parts throughout the drawings. Also, it is understood that the depictions in the figures are diagrammatic and not necessarily to scale.

DETAILED DESCRIPTION OF EMBODIMENTS OF THE INVENTION

In one embodiment of the invention, methods of reducing crosstalk in a structural health monitoring system are described. A pair of actuator input signals are sent to an actuator, each resulting in the transmission of stress waves to a corresponding sensor. The sensor then converts these stress waves to a pair of output signals, each having a crosstalk portion due to electromagnetic interference from the input signals to the actuator, and a stress wave portion corresponding to the stress waves. Various methods of varying the actuator input signals, the input to the actuator, and the output of the sensor result in two output signals that can be combined so as to reduce the crosstalk portions and isolate the stress wave portions. This allows actuators and sensors to be placed sufficiently close together that the stress wave portions of sensor output signals can overlap their crosstalk, without corrupting or otherwise compromising the data contained therein.

Figure 1:
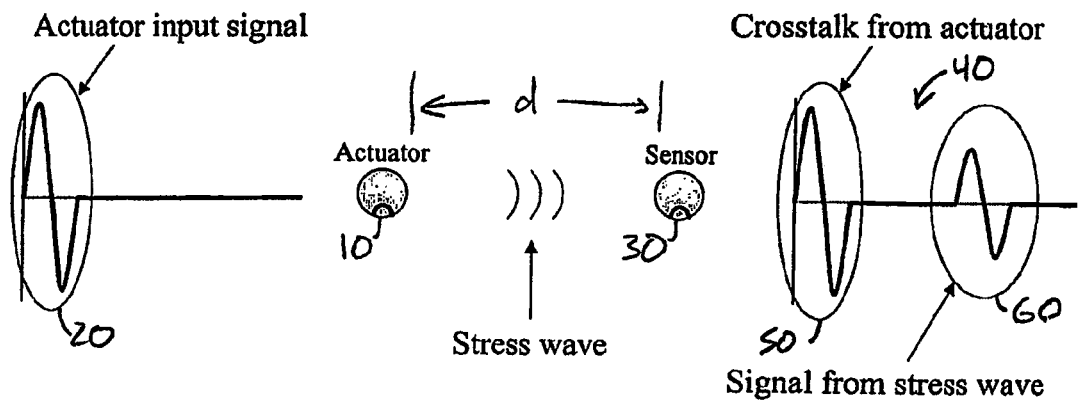
FIG. 1 illustrates crosstalk in a conventional actuator and sensor system used in structural health monitoring.
Figure 2:
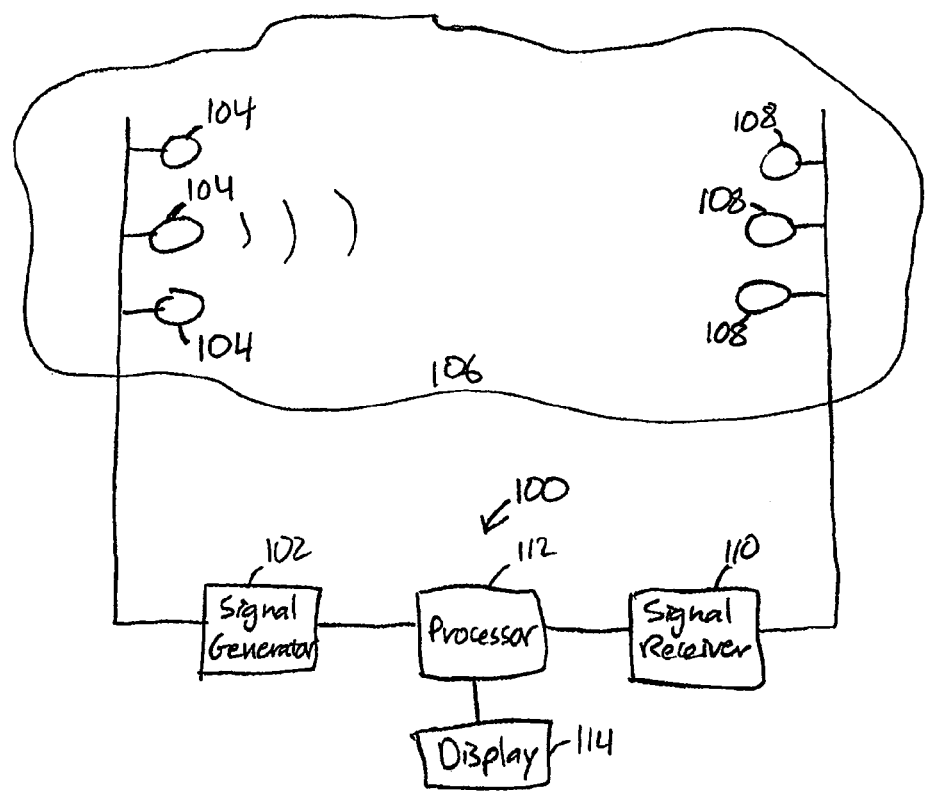
FIG. 2 illustrates a structural health monitoring system for reducing crosstalk according to an embodiment of the present invention.

FIG. 2 illustrates an exemplary structural health monitoring system for reducing crosstalk according to an embodiment of the present invention. A structural health monitoring system 100 includes a signal generator 102 capable of transmitting signals to actuators 104. These actuators 104 convert the signals from the signal generator 102 to stress waves that propagate through the structure 106 to sensors 108, where they are converted back to signals detected by the signal receiver 110. The signal receiver 110 conditions and amplifies these signals as necessary, and passes them on to the processor 112, where they are analyzed and manipulated as appropriate. The results are then sent to the display 114.

In operation, two signals can be transmitted to one or more of the actuators 104. Each of these signals generates crosstalk as output from the sensors 108 to the receiver 110. Each of these signals also causes the actuators 104 to generate stress waves that are detected by the sensors 108 and output as additional signals to the receiver 110. Thus, each signal that is input to the actuators 104 causes an output to the receiver 110 that has two portions: a crosstalk portion due to electromagnetic interference from the input signal, and a stress wave portion corresponding to the stress waves detected by the sensors 108 and converted into signals.

One of ordinary skill in the art will realize that different embodiments of the invention can employ different types of actuators 104 and sensors 108. For example, in the embodiments described below, the actuators 104 and sensors 108 can be known piezoelectric transducers capable of reacting to a propagating stress wave by generating a voltage signal. In such an embodiment, and when affixed to a structure, each actuator 104 and sensor 108 is a sensor/actuator capable of both converting an electrical voltage signal to a stress wave, and converting the stress wave back to a voltage so that the properties of the wave, and thus the structure, can be analyzed. These sensor/actuators are often fabricated as three-terminal elements where the voltage is generated/applied across a negative terminal and one of two positive terminals, so that the positive and negative terminals can be switched. However, one of ordinary skill in the art will realize that the invention is not limited to these embodiments, and can encompass the use of any type of actuator and/or sensor, such as fiber optic transducers and the like, which can be used to generate signals that can be combined so as to reduce crosstalk.

The invention can also employ actuators 104 and sensors 108 that are placed on a flexible dielectric substrate to form a diagnostic layer. Such diagnostic layers can offer advantages over groups of individual actuators 104 and sensors 108, in that a single layer is often easier to attach than multiple actuators 104 and sensors 108. Diagnostic layers often provide a convenient way of grouping the wires of the actuators 104 and sensors 108 in a more easily handled manner. Such diagnostic layers and their operation are further described in, for example, U.S. Pat. No. 6,370,964 to Chang et al., which is hereby incorporated by reference in its entirety and for all purposes. Construction of these diagnostic layers is also explained in U.S. patent application Ser. No. 10/873,548, filed on Jun. 21, 2004, which is also incorporated by reference in its entirety and for all purposes. However, it should be noted that the present invention is not limited to the diagnostic layers disclosed in the aforementioned U.S. patent application Ser. No. 10/873,548, and indeed need not use them at all. Rather, any sensors and actuators can be employed, regardless of whether they are incorporated into a flexible substrate or not. The invention simply contemplates sensors and actuators that are attached to structures in any manner that allows for analysis according to the methods described herein. One of skill will realize that many different approaches exist for attaching sensors and actuators to a structure, not all of which employ flexible substrates.

Figure 3:
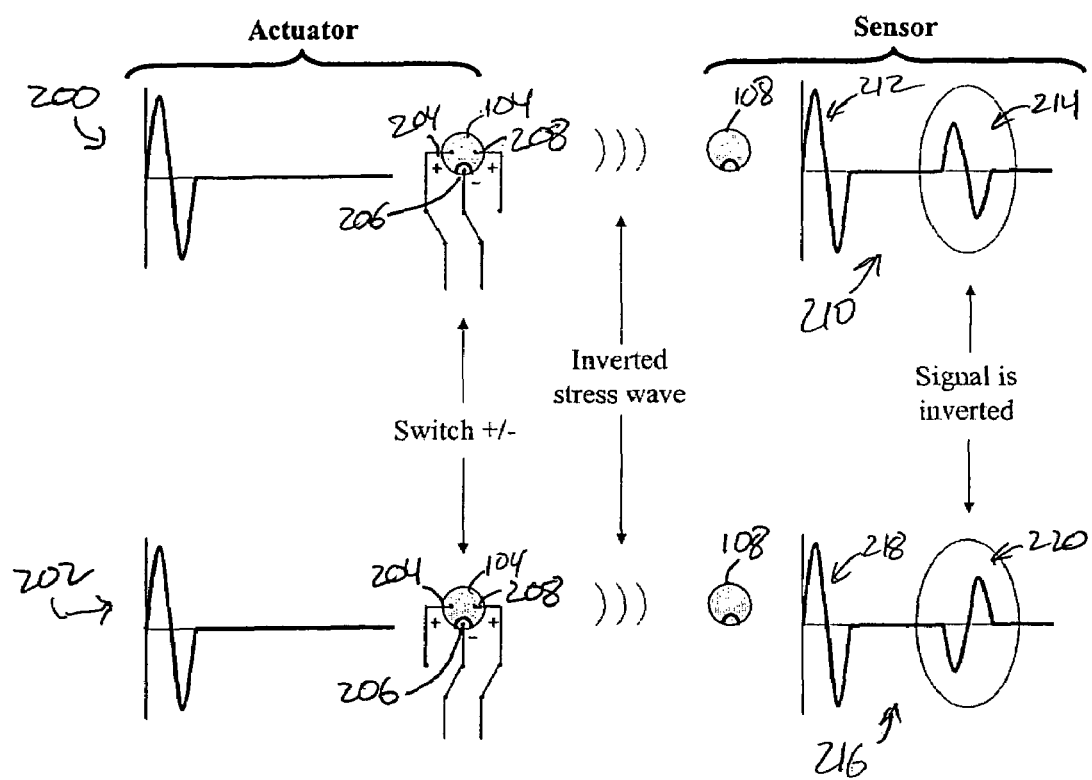
FIG. 3 illustrates a first method for reducing crosstalk according to an embodiment of the present invention.

The invention includes various ways of combining these signals so as to reduce the crosstalk and isolate the stress wave portions of the output signals. FIG. 3 illustrates a first such method. Here, two substantially identical input signals 200, 202 are sent to an actuator 104, but the leads of the actuator 104 are switched for the second input signal 202. That is, the first input signal 200 is transmitted to the actuator 104 through positive terminal 204 and negative terminal 206. This generates a stress wave that is detected by the sensor 108 and converted into an output signal 210 that has a crosstalk portion 212 due to electromagnetic interference from the input signal 200, and a stress wave portion 214 from the detected stress wave. The leads to the actuator 104 are then switched (i.e., its input is inverted), so that the second input signal 202 is transmitted to the actuator 104 through positive terminal 208 and negative terminal 206, while positive terminal 204 goes unused. This causes the actuator 104 to generate an inverted stress wave that is detected by the sensor 108 and converted into an output signal 216 with a crosstalk portion 218 and stress wave portion 220. Note that the crosstalk portion 218 of the second input signal 202 is substantially identical to the crosstalk portion 212 of the first input signal 200, however the stress wave portion 220 of the second input signal 202 is inverse to the stress wave portion 214 of the first input signal 200. The two output signals 210, 216 can then be subtracted, reducing or eliminating the crosstalk portions 212, 218 and therefore isolating the stress wave portions 214, 220.

One of ordinary skill in the art will realize that this method of the invention allows the crosstalk portions 212, 218 to be isolated from the stress wave portions 214, 220 even when the portions overlap, allowing actuators 104 and sensors 108 to be placed closer than distance $d_{min}$ apart without fear of crosstalk corrupting or otherwise compromising structural health monitoring data.

Figure 4:
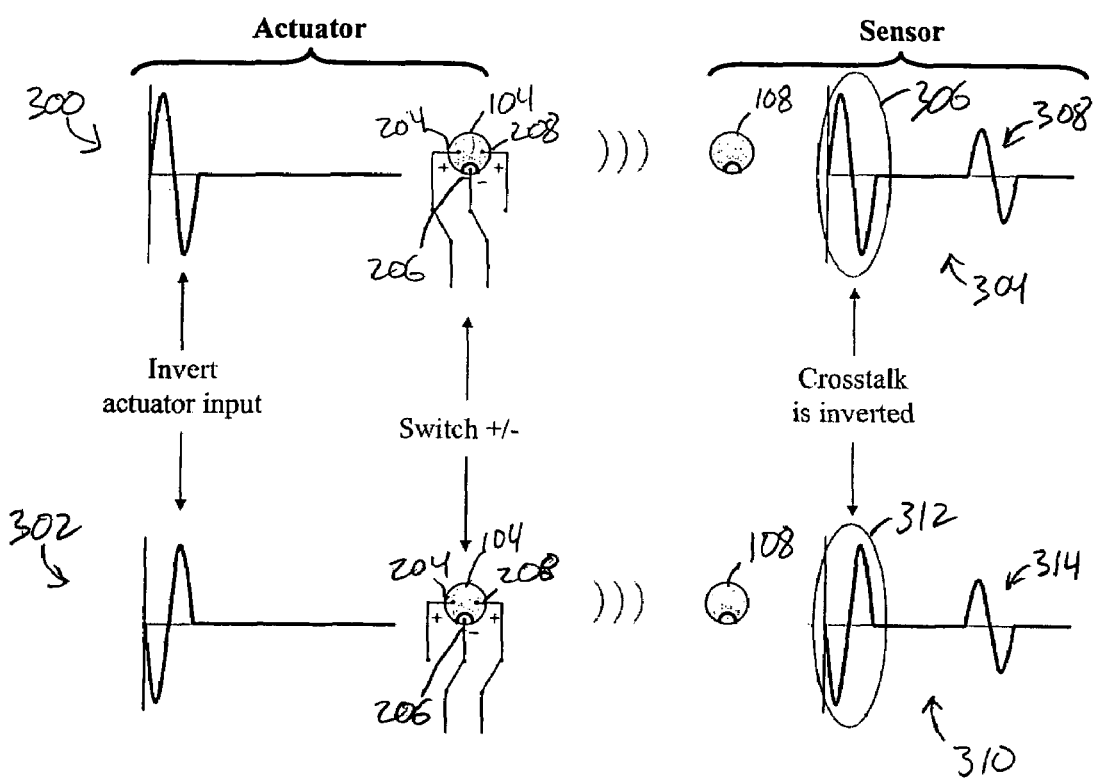
FIG. 4 illustrates a second method for reducing crosstalk according to an embodiment of the present invention.

FIG. 4 illustrates a second such method in accordance with embodiments of the invention. Here, two generally inverted input signals 300, 302 are sent to the actuator 104, and the leads of the actuator 104 are also switched for the second input signal 302. The resulting crosstalk signals are thus inverted, while the signals corresponding to the stress wave are not. More specifically, the first input signal 300 is transmitted to the actuator 104 through positive terminal 204 and negative terminal 206. This generates a stress wave that is detected by the sensor 108 and converted into an output signal 304 that has a crosstalk portion 306 and stress wave portion 308 as shown. The leads to the actuator 104 are then switched, so that the second input signal 302 are transmitted to the actuator 104 through positive terminal 208 and negative terminal 206. This causes the actuator 104 to generate an inverted stress wave that is detected by the sensor 108 and converted into an output signal 310 with a crosstalk portion 312 and stress wave portion 314. Done in this manner, the crosstalk portion 306 of the first input signal 300 is substantially inverse to the crosstalk portion 312 of the second input signal 302, while the two corresponding stress wave portions 308, 314 are substantially identical. Accordingly, the two output signals 304, 310 can be added, reducing or eliminating the crosstalk portions 306, 312 and isolating the stress wave portions 308, 314.

Figure 5:
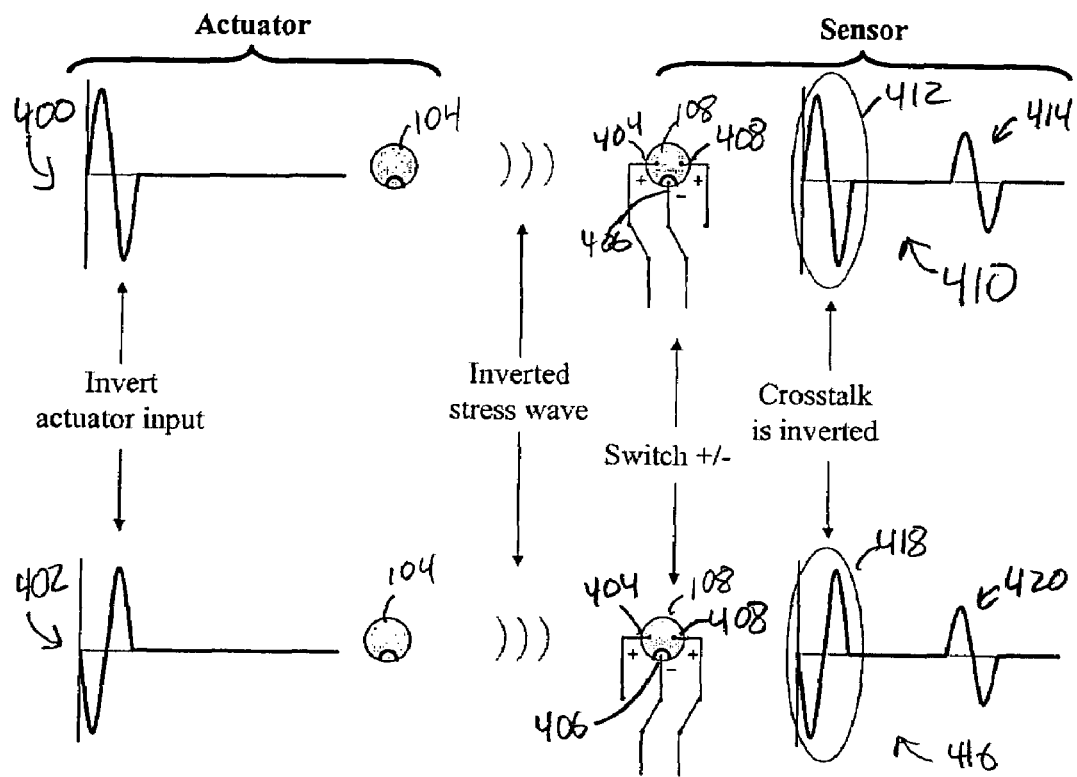
FIG. 5 illustrates a third method for reducing crosstalk according to an embodiment of the present invention.

FIG. 5 illustrates a third such method of the invention. Here, two generally inverted input signals 400, 402 are sent to an actuator 104, and the leads from the sensor 108 are switched (i.e., its output is inverted) for the second input signal 402. The resulting crosstalk signals are inverted, while the signals corresponding to the detected stress waves are not. That is, the first input signal 400 is sent to the actuator 104, where it is converted to stress waves. These waves are detected by the sensor 108, where they are converted to an output signal 410 having a crosstalk portion 412 and stress wave portion 414. This output signal is transmitted to the receiver 110 via terminals 404 and 406. The leads from the sensor 108 are then switched, and the second output signal 402 is transmitted to the actuator 104. This signal 402 is substantially inverse to the first input signal 400, resulting in an inverted stress wave sent to the sensor 108. As the leads from the sensor 108 are switched, the resulting signal is sent to the receiver 110 from terminals 406 and 408, while terminal 404 goes unused. As the second input signal 402 is approximately inverse to the first input signal 400, the resulting output signal 416 has a crosstalk portion 418 that is approximately inverse to the crosstalk portion 412. However, because the leads from sensor 108 are also switched, the stress wave portions 414, 420 are roughly identical, and not inverse. Accordingly, the two output signals 410, 416 can be added, reducing or eliminating the crosstalk portions 412, 418 and isolating the stress wave portions 414, 420.

Figure 6:
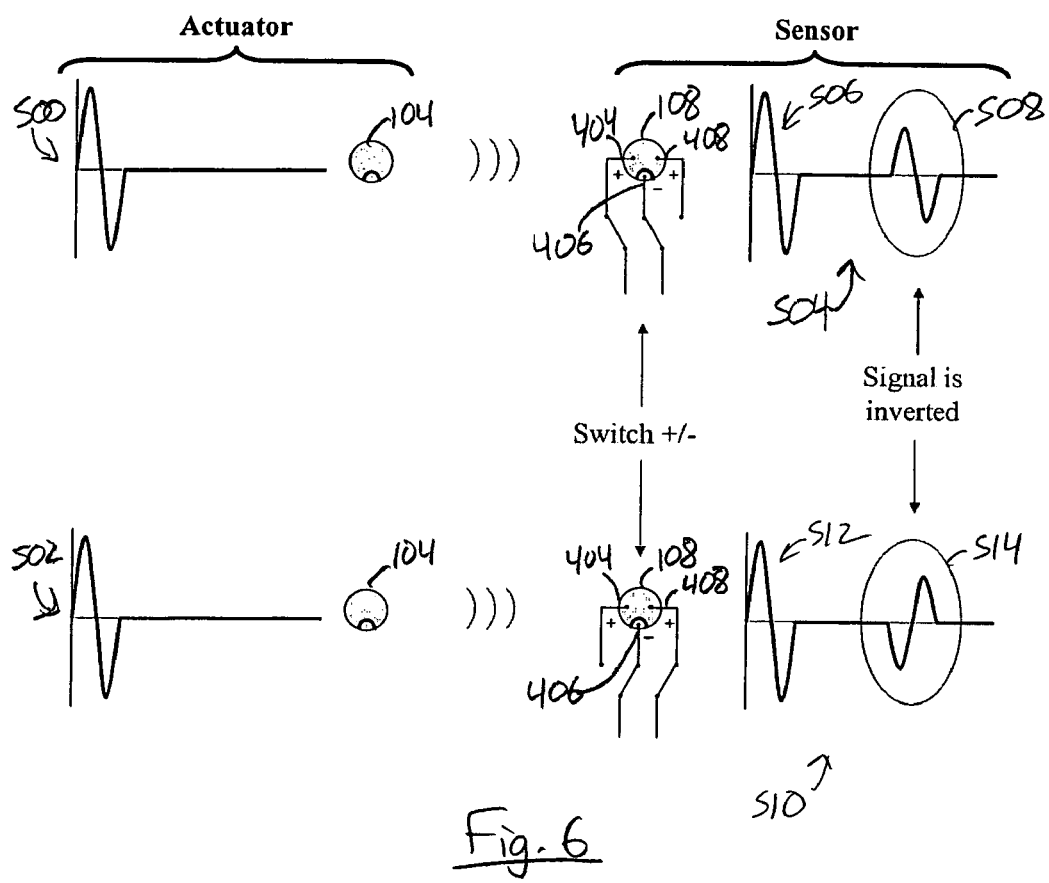
FIG. 6 illustrates a fourth method for reducing crosstalk according to an embodiment of the present invention.

FIG. 6 illustrates a fourth such method of the invention. Here, two roughly identical input signals 500, 502 are sent to an actuator 104, and the leads from the sensor 108 are switched for the second input signal 502. The resulting signals corresponding to the detected stress waves are thus inverted, while the crosstalk for each remains the same. More specifically, the first input signal 500 is sent to the actuator 104, where it is converted to stress waves. These waves are detected by the sensor 108, where they are converted to an output signal 504 having a crosstalk portion 506 and a stress wave portion 508. The output signal 504 is sent to the receiver 110 via terminals 404, 406. The leads from the sensor 108 are then switched, and the second output signal 502 is transmitted to the actuator 104. This signal 502 is substantially identical to the first input signal 500. As the leads from the sensor 108 are switched, the resulting output signal 510 is sent to the receiver 110 from terminals 406 and 408 with a crosstalk portion 512 that is substantially identical to the crosstalk portion 506 caused by the first input signal 500, while the stress wave portion 514 is inverted. Thus, the two output signals 504, 510 can be subtracted, reducing or eliminating the crosstalk portions 506, 512 while isolating the stress wave portions 508, 514.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, the invention can be utilized to reduce crosstalk in structural health monitoring systems employing any type of sensor, actuator, and/or sensor/actuator, such as piezoelectric sensor/actuators, fiber optic transducers, and the like, so long as the output signals from such sensing elements can be combined so as to reduce or eliminate crosstalk. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of facilitating structural health monitoring according to stress waves transmitted from an actuator to a sensor through the structure, comprising:
    initiating the transmission of first and second actuation signals to the actuator so as to facilitate the generation of first and second stress waves within the structure;
    receiving first and second sensor signals from the sensor, the sensor signals each having a crosstalk portion corresponding to an electromagnetic interference from the respective actuation signal, and a stress wave portion corresponding to the respective stress wave, wherein the crosstalk portion of each sensor signal overlaps the stress wave portion of that sensor signal; and
    combining the first and second sensor signals so as to isolate the stress wave portions from the crosstalk portions.

2. The method of claim 1 wherein:
    the initiating further comprises initiating the transmission of the second actuation signal, the second actuation signal being approximately identical to the first actuation signal;
    the receiving further comprises inverting an output of the sensor so as to receive the second sensor signal, the stress wave portion of the second sensor signal being approximately inverse to the stress wave portion of the first sensor signal and the crosstalk portion of the second sensor signal being approximately identical to the crosstalk portion of the first sensor signal; and
    the combining further comprises subtracting the first and second sensor signals so as to isolate the stress wave portions from the crosstalk portions.

3. The method of claim 1 wherein:
    the initiating further comprises initiating the transmission of the second actuation signal, the second actuation signal being approximately inverse to the first actuation signal;

the receiving further comprises inverting an output of the sensor so as to receive the second sensor signal, the crosstalk portion of the second sensor signal being approximately inverse to the crosstalk portion of the first sensor signal and the stress wave portion of the second sensor signal being approximately identical to the stress wave portion of the first sensor signal; and the combining further comprises adding the first and second sensor signals so as to isolate the stress wave portions from the crosstalk portions.

4. The method of claim 1 wherein:

the initiating further comprises, after initiating the transmission of the first actuation signal, inverting an output of the actuator and subsequently initiating the transmission of the second actuation signal, the second actuation signal being approximately identical to the first actuation signal;

the receiving further comprises receiving the second sensor signal, the stress wave portion of the second sensor signal being approximately inverse to the stress wave portion of the first sensor signal and the crosstalk portion of the second sensor signal being approximately identical to the crosstalk portion of the first sensor signal; and the combining further comprises subtracting the first and second sensor signals so as to isolate the stress wave portions from the crosstalk portions.

5. The method of claim 1 wherein:

the initiating further comprises, after initiating the transmission of the first actuation signal, inverting an output of the actuator and subsequently initiating the transmission of the second actuation signal, the second actuation signal being approximately inverse to the first actuation signal;

the receiving further comprises receiving the second sensor signal, the crosstalk portion of the second sensor signal being approximately inverse to the crosstalk portion of the first sensor signal and the stress wave portion of the second sensor signal being approximately identical to the stress wave portion of the first sensor signal; and the combining further comprises adding the first and second sensor signals so as to isolate the stress wave portions from the crosstalk portions.

6. A computer readable medium encoded with computer executable instructions thereon for a method of monitoring the health of a structure according to stress waves transmitted from an actuator to a sensor through the structure, the method comprising:

initiating the transmission of first and second actuation signals to the actuator so as to facilitate the generation of first and second stress waves within the structure;

receiving first and second sensor signals from the sensor, the sensor signals each having a crosstalk portion corresponding to an electromagnetic interference from the respective actuation signal, and a stress wave portion corresponding to the respective stress wave, wherein the crosstalk portion of each sensor signal overlaps the stress wave portion of that sensor signal; and combining the first and second sensor signals so as to isolate the stress wave portions from the crosstalk portions.

7. The computer readable medium of claim 6 wherein:

the initiating further comprises initiating the transmission of the second actuation signal, the second actuation signal being approximately identical to the first actuation signal;

the receiving further comprises inverting an output of the sensor so as to receive the second sensor signal, the stress wave portion of the second sensor signal being approximately inverse to the stress wave portion of the first sensor signal and the crosstalk portion of the second sensor signal being approximately identical to the crosstalk portion of the first sensor signal; and the combining further comprises subtracting the first and second sensor signals so as to isolate the stress wave portions from the crosstalk portions.

8. The computer readable medium of claim 6 wherein:

the initiating further comprises initiating the transmission of the second actuation signal, the second actuation signal being approximately inverse to the first actuation signal;

the receiving further comprises inverting an output of the sensor so as to receive the second sensor signal, the crosstalk portion of the second sensor signal being approximately inverse to the crosstalk portion of the first sensor signal and the stress wave portion of the second sensor signal being approximately identical to the stress wave portion of the first sensor signal; and the combining further comprises adding the first and second sensor signals so as to isolate the stress wave portions from the crosstalk portions.

9. The computer readable medium of claim 6 wherein:

the initiating further comprises, after initiating the transmission of the first actuation signal, inverting an output of the actuator and subsequently initiating the transmission of the second actuation signal, the second actuation signal being approximately identical to the first actuation signal;

the receiving further comprises receiving the second sensor signal, the stress wave portion of the second sensor signal being approximately inverse to the stress wave portion of the first sensor signal and the crosstalk portion of the second sensor signal being approximately identical to the crosstalk portion of the first sensor signal; and the combining further comprises subtracting the first and second sensor signals so as to isolate the stress wave portions from the crosstalk portions.

10. The computer readable medium of claim 6 wherein:

the initiating further comprises, after initiating the transmission of the first actuation signal, inverting an output of the actuator and subsequently initiating the transmission of the second actuation signal, the second actuation signal being approximately inverse to the first actuation signal;

the receiving further comprises receiving the second sensor signal, the crosstalk portion of the second sensor signal being approximately inverse to the crosstalk portion of the first sensor signal and the stress wave portion of the second sensor signal being approximately identical to the stress wave portion of the first sensor signal; and the combining further comprises adding the first and second sensor signals so as to isolate the stress wave portions from the crosstalk portions.

11. A system for facilitating structural health monitoring, comprising:

an actuator configured to generate a stress wave from an actuation signal;

a sensor configured to receive the stress wave and to generate a sensor signal having a first portion corresponding to an electromagnetic interference from the actuation signal, and a second portion corresponding to the stress wave; and a processor in communication with the actuator and the sensor;

wherein the actuator and the sensor are configured for placement upon a structure at a distance apart from each other, the distance corresponding to the second portion of the sensor signal overlapping the first portion; and wherein the processor is configured to isolate the second portion of the sensor signal from the overlapping first portion.

12. The system of claim 11 wherein the processor is further configured to:
    initiate the transmission of first and second actuation signals to the actuator so as to facilitate the generation of first and second stress waves within the structure;
    receive first and second sensor signals from the sensor, the sensor signals each having a crosstalk portion corresponding to an electromagnetic interference from the respective actuation signal, and a stress wave portion corresponding to the respective stress wave; and
    combine the first and second sensor signals so as to isolate the stress wave portions from the crosstalk portions.

13. The system of claim 12 wherein the processor is further configured to:
    initiate the transmission of the second actuation signal, the second actuation signal being approximately identical to the first actuation signal;
    invert an output of the sensor so as to receive the second sensor signal, the crosstalk portion of the second sensor signal being approximately identical to the crosstalk portion of the first sensor signal; and
    subtract the first and second sensor signals so as to isolate the stress wave portions from the crosstalk portions.

14. The system of claim 12 wherein the processor is further configured to:
    initiate the transmission of the second actuation signal, the second actuation signal being approximately inverse to the first actuation signal;
    invert an output of the sensor so as to receive the second sensor signal, the second sensor signal having a crosstalk portion approximately inverse to the crosstalk portion of the first sensor signal; and
    add the first and second sensor signals so as to isolate the stress wave portions from the crosstalk portions.

15. The system of claim 12 wherein the processor is further configured to:
    after initiating the transmission of the first actuation signal, invert an output of the actuator so as to transmit the second actuation signal, the second actuation signal being approximately identical to the first actuation signal;
    receive the second sensor signal from the sensor, the crosstalk portion of the second sensor signal being approximately identical to the crosstalk portion of the first sensor signal; and
    subtract the first and second sensor signals so as to isolate the stress wave portions from the crosstalk portions.

16. The system of claim 12 wherein the processor is further configured to:
    after initiating the transmission of the first actuation signal, invert an output of the actuator and subsequently transmit the second actuation signal, the second actuation signal being approximately inverse to the first actuation signal;
    invert an output of the sensor so as to receive the second sensor signal, the crosstalk portion of the second sensor signal being approximately inverse to the crosstalk portion of the first sensor signal; and
    add the first and second sensor signals so as to isolate the stress wave portions from the crosstalk portions.

* * * * *

UNITED STATES PATENT AND TRADEMARK OFFICE
CERTIFICATE OF CORRECTION

PATENT NO. : 7,596,078 B2  Page 1 of 1
APPLICATION NO. : 11/271351
DATED : September 29, 2009
INVENTOR(S) : Beard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 900 days.

Signed and Sealed this

Twenty-eighth Day of September, 2010

David J. Kappos
*Director of the United States Patent and Trademark Office*